United States Patent [19]

Schwindeman

[11] Patent Number: 4,756,744
[45] Date of Patent: Jul. 12, 1988

[54] HERBICIDALLY ACTIVE 4-AMINOALKYLAMINO-3-ISOXAZOLYL-2-IMIDAZOLIDINONE DERIVATIVES

[75] Inventor: James A. Schwindeman, Fairlawn, Ohio

[73] Assignee: PPG Industries, Inc., Pittsburgh, Pa.

[21] Appl. No.: 748,066

[22] Filed: Jun. 24, 1985

[51] Int. Cl.$^4$ .................... A01N 43/50; A01N 43/80; C07D 233/22

[52] U.S. Cl. ........................................ 71/92; 548/245; 548/246; 548/318; 548/319

[58] Field of Search ............... 548/317, 318, 319, 245, 548/246; 71/92

[56] References Cited

U.S. PATENT DOCUMENTS 4,345,936  8/1982  Thibault et al. ..................... 548/319
4,426,527  1/1984  Lavanish et al. ..................... 548/133
4,707,180 11/1987  Schwindeman ..................... 548/246

FOREIGN PATENT DOCUMENTS 2543552  5/1984  France ............................... 548/246

OTHER PUBLICATIONS

Hatzios et al., *Metabolism of Herbicides in Higher Plants*, Burgess Publishing, (1982), Minneapolis, p. 5.

*Primary Examiner*—Donald G. Daus
*Assistant Examiner*—Mark W. Noel
*Attorney, Agent, or Firm*—Edward J. Whitfield

[57] ABSTRACT

The invention relates to certain 3-isoxazolyl-2-imidazolidinone derivatives, namely 3-[5- or 3-substituted-3- or 5-isoxazolyl]-1-substituted-4-substituted amino-2-imidazolidinones and the uses thereof for preemergence or postemergence control of noxious plants, i.e., weeds.

4 Claims, No Drawings

HERBICIDALLY ACTIVE 4-AMINOALKYLAMINO-3-ISOXAZOLYL-2-IMIDAZOLIDINONE DERIVATIVES

FIELD OF THE INVENTION

This invention relates to certain 3-isoxazolyl-2-imidazolidinone derivatives, namely 3-[5- or 3-substituted-3- or 5-isoxazolyl]-1-substituted-4-substituted amino-2-imidazolidinones and the use thereof for preemergence or postemergence control of noxious plants, i.e., weeds.

DESCRIPTION OF THE INVENTION

This invention provides herbicidally active 3-[5- or 3- or substituted -3 or -5-isoxazolyl]-1-substituted-4-substituted amino-2-imidazolidinones represented by the Formula I:

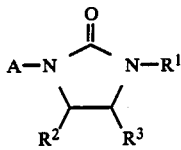

wherein
A is

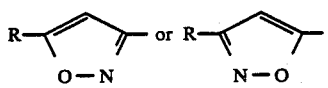

wherein: R is selected from up to $C_6$ alkyl, haloalkyl or cycloalkyl, up to $C_5$ alkenyl or alkynyl, —$R^5$—O—$R^6$ or —$R^5$—S—$R^6$ wherein $R^5$ is up to $C_6$ alkylene and $R^6$ is up to $C_6$ alkyl or optionally substituted phenyl or benzyl;
$R^1$ is up to $C_3$ alkyl or allyl;
$R^2$ and $R^3$ are selected from hydrogen, hydroxy or

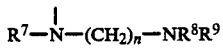

with the proviso that one of $R^2$ or $R^3$ must be

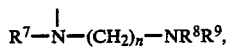

$R^7$ is hydrogen or up to $C_6$ alkyl or haloalkyl, acyl or aryl;
$R^8$ and $R^9$ are the same or different and are selected from hydrogen, up to $C_6$ alkyl, haloalkyl or alkoxyalkyl, aryl, alkylcarbonyl, aminocarbonyl or carboxy, or $R^8$ and $R^9$ together form up to a 6-membered heterocyclic ring containing up to 3 hetero atoms; and
n is 2, 3, 4 or 5

Although any compound within the scope of Formula I is believed to have herbicidal activity, preferred compounds are those wherein R is alkyl, especially tertiary butyl, $R^1$ is alkyl, especially methyl and $R^2$ is

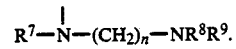

The compounds of this invention can be readily synthesized using available starting materials, such as the isoxazolyl-imidazolidinone compounds described in U.S. Pat. No. 4,268,679 and using techniques known to the art. For example, the compounds of this invention may be prepared by reacting an isoxazolyl-imidazolidinone compound of the formula:

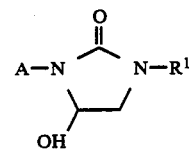

wherein A and $R^1$ are as previously defined with a suitably substituted amine of the formula, $R^7$—N-H—$(CH_2)_n$—$NR^8 R^9$, wherein $R^7$, $R^8$, $R^9$ and n are as previously defined. The reaction is typically conducted in an inert organic solvent medium at up to reflux temperature and usually in the presence of a strong mineral or organic acid, e.g., p-toluenesulfonic acid.

The following Examples are illustrative of the preparation of certain specific compounds of this invention.

EXAMPLE I

Preparation of:
3-[5-(t-butyl)-3-isoxazolyl]-1-methyl-4-[N-(2-dimethylamino)ethyl]amino-2-imidazolidinone To 50 milliliter flask provided with a magnetic stirring bar and a reflux condenser were charged 2.39 grams (0.01 mole) of 3-[5-(t-butyl)-3-isoxazolyl]-1-methyl-4-hydroxy-2-imidazolidinone, 1.32 grams (0.015 mole) of N-(2-(dimethylamino)ethyl)amine, 0.1 gram of p-toluenesulfonic acid and 12 milliliters of dry toluene. The resulting tan mixture was heated to 80° C. and maintained at 80° C. for 3 hours at which time TLC analysis indication complete conversion of starting materials. The reaction mixture was then cooled to room temperature, transferred to a separatory funnel, diluted with 100 milliliters of ethyl acetate, and washed consecutively with 100 milliliter portions of saturated aqueous sodium bicarbonate and saturated aqueous sodium chloride. The organic layer was drawn off, dried over anhydrous magnesium sulfate, filtered and concentrated in vacuo affording 2.95 grams of material, confirmed by NMR analysis as the desired product.

EXAMPLE II

Preparation of:
3-[5-(t-butyl)-3-isoxazolyl]-1-methyl-4-[N-(2-amino)ethyl]amino-2-imidazolidinone To 50 milliliter flask provided with a magnetic stirring bar, a Dean-Stark trap and a reflux condenser were charged 2.39 grams (0.01 mole) of 3-[5-(t-butyl)-3-isoxazolyl]-1-methyl-4-hydroxy-2-imidazolidinone, 0.9 gram (0.015 mole) of N-(2-aminoethyl)amine, 0.17 gram of p-toluene-sulfonic acid and 10 milliliters of dry toluene. The resulting golden solution was heated to reflux and maintained at reflux for 2 hours, at which time TLC analysis indicated complete conversion of starting materials. The reaction mixture was then cooled to room temperature, transferred to a separatory funnel, diluted with 100 milliliters of ethyl acetate and washed consecutively with 100 milliliter portions of saturated aqueous sodium bicarbonate and saturated aqueous sodium chloride. The organic layer was drawn-off, dried over anhydrous sodium sulfate, filtered and concentrated in vacuo affording 1.93 grams of golden oil, confirmed by NMR analysis as the desired product.

EXAMPLE III

Preparation of:
3-[5-(t-butyl)-3-isoxazolyl]-1-methyl-4-[N-methyl-N-(2-aminoethyl)]amino-2-imidazolidinone To a 50 milliliter flask provided with a magnetic stirring bar, a reflux condenser and a drying tube were charged 2.39 grams (0.01 mole) of 3-[5-(t-butyl)-3-isoxazolyl]-1-methyl-4-hydroxy-2-imidazolidinone, 0.15 gram of p-toluenesulfonic acid and 10 milliliters of dry toluene. 1.11 Gram (0.015 mole) of N-[2-(ethylamino)ethyl]amine was added via a syringe. The resulting pale yellow mixture was heated to 70° C. and maintained at 70° C. for 4 hours, at which time TLC analysis indicated complete consumption of starting material. The reaction mixture was cooled to room temperature, transferred to a separatory funnel, diluted with 100 milliliters of ethyl acetate and washed consecutively with 100 milliliter portion of saturated aqueous sodium bicarbonate and saturated aqueous sodium chloride. The organic layer was drawn-off, dried over anhydrous magnesium sulfate, filtered and concentrated in vacuo affording 1.21 grams of golden oil, confirmed by NMR analysis as the desired product.

EXAMPLE IV

Preparation of:
3-[5-(t-butyl)-3-isoxazolyl]-1-methyl-4-[N-(methyl)-N-[(2-methylamino)ethyl]amino-2-imidazolidinone To a 50 milliliter flask provided with a magnetic stirring bar and a drying tube were charged 2.39 grams (0.01 mole) of 3-[5-(t-butyl)-3-isoxazolyl]-1-methyl-4-hydroxy-2-imidazolidinone, 0.17 gram of p-toluenesulfonic acid, 10 milliliters of dry toluene and finally 2.0 grams (0.0227 mole of [N-(methyl)-N-(2-methylamino)ethyl]amine. After stirring at room temperature for 48 hours, the reaction mixture was heated to 80° C. and maintained at 80° C. for 4 hours, at which time TLC analysis indicated complete consumption of starting material. The reaction mixture was cooled to room temperature, transferred to a separatory funnel, diluted with 100 milliliters of ethyl acetate and washed consecutively with 100 milliliter portions of saturated aqueous sodium bicarbonate and saturated aqueous sodium chloride. The organic layer was drawn-off, dried over anhydrous sodium sulfate, filtered and concentrated in vacuo affording 1.78 grams of golden oil confirmed by NMR analysis as the desired product.

EXAMPLE V

Preparation of:
3-[5-(t-butyl)-3-isoxazolyl]-1-methyl-4-[N-(2-diethylamino)ethyl]amino-2-imidazolidinone To a 50 milliliter flask provided with a magnetic stirring bar, a Dean-Stark trap and a reflux condenser were charged 2.39 grams (0.01 mole) of 3-[5-(t butyl)-3-isoxazolyl]-1-methyl-4-hydroxy-2-imidazolidinone, 1.75 grams (0015 mole) of N-(2-diethylaminoethyl)amine, 0.14 gram of p-toluenesulfonic acid and 12 milliliters of dry toluene. The stirred reaction mixture was heated to gentle reflux and maintained at reflux for 2 hours, at which time TLC analysis indicated complete consumption of starting material. The reaction mixture was cooled to room temperature, transferred to a separatory funnel, diluted with 120 milliliters of ethyl acetate and washed with a 100 milliliter portion of saturated aqueous sodium bicarbonate. The organic layer was decanted-off and the aqueous layer was back extracted with 2×100 milliliter portions of ethyl acetate. The combined organic over anhydrous magnesium sulfate, filtered and concentrated in vacuo, affording 3.25 grams of orange oil confirmed by NMR analysis as the desired product.

EXAMPLE VI

Preparation of:
3-[5-(t-butyl)-3-isoxazolyl]-1-methyl-4-[N-(2-acetylamino)ethyl]amino-2-imidazolidinone To a 50 milliliter flask provided with a magnetic stirring bar, a Dean-Stark trap and a reflux condenser were charged 2.39 grams (0.01 mole) of 3-[5-(t-butyl)-3-isoxazolyl]-1-methyl-4-hydroxy-2-imidazolidinone, 0.15 gram of p-toluenesulfonic acid, 12 milliliters of toluene and, finally, 1.53 grams (0.015 mole) of N-[2-(acetylamino)ethyl]amine. The mixture was heated to reflux and maintained at reflux for 5 hours, at which time TLC analysis indicated complete consumption of starting material. The reaction mixture was cooled to room temperature, transferred to a separatory funnel, washed with a 100 milliliter portion of saturated aqueous sodium bicarbonate and diluted with 100 milliliters of ethyl acetate. The organic layer was decanted-off and the aqueous layer was backed extracted with 2×100 milliliter portions of ethyl acetate. The combined organic layers were dried over anhydrous magnesium sulfate, filtered and concentrated in vacuo, affording 3.17 grams of golden oil confirmed by NMR analysis as the desired product.

EXAMPLE VII

Preparation of:
3-[5-(t-butyl)-3-isoxazolyl]-1-methyl-4-[N-(2-aminoethyl)-N-ethyl]amino-2-imidazolidinone To a 50 milliliter flask provided a magnetic stirring bar, a Dean-Stark trap and a reflux condenser were charged 2.39 grams (0.01 mole) of 3-[5-(t-butyl)-3-isoxazolyl]-1-methyl-4-hydroxy-2-imidazolidinone, 0.14 gram of p-toluenesulfonic acid, 10 milliliters of toluene and 1.33 gram (0.015 mole) of N-[(2-ethylamino)ethyl]amine. The reaction mixture was heated to reflux and maintained at reflux for 4 hours, at which time TLC analysis indicated complete consumption starting material. The reaction mixture was cooled to room temperature, transferred to a separatory funnel, diluted with 100 milliliters of ethyl acetate and washed with a 100 milliliter portion of saturated aqueous sodium bicarbonate. The organic layer was drawn-off and the aqueous layer was back extracted with 2×100 milliliter portions of ethyl acetate. The combined organic layers were dried over anhydrous magnesium sulfate, filtered and concentrated in vacuo affording 2.83 grams of orange oil confirmed by NMR analysis as the desired product.

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre, e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.01 to 2.0 pounds per acre.

Of course, a compound of this invention can be formulated according to routine methods with any of several known and commonly used herbicidal diluents, adjuvants and carriers. The formulations can contain liquid carriers and adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surfaced applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention could be used for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail, ironweed, sesbania, cattail, wintercress, horsenettle, nutsedge, milkweed, sicklepod, and the like.

The compounds prepared as described in the Examples were individually tested for herbicidal efficacy against a variety of broadleaf and grassy weed species, under controlled laboratory conditions of light, humidity and temperature. A solvent solution of each compound was applied, both preemergence and postemergence, to test flats containing the various weed species, and herbicidal efficacy was determined by periodic visual inspection vis a vis an untreated control. Herbicidal efficacy was determined on a Numerical Injury Rating (NIR) scale of from 0 (no injury) to 10 (all plants dead). A NIR rating of 7-9 indicates severe injury; a NIR rating of 4-6 indicates moderate injury, i.e., plant growth is reduced to the extent that normal growth would be expected only under ideal conditions; and a NIR rating of 1-3 indicates slight injury.

The following table gives the average preemergence and postemergence NIR determined for each of the compounds prepared as described in Examples I to VII on the broadleaf (BL) and grassy (GR) weed species to which the compounds were applied. The compounds of Examples I to VII were each applied at a rate of 0.5 pound per acre and the NIR was determined three weeks subsequent to application.

|         | I   | II  | III | IV  | V   | VI  | VII |
|---------|-----|-----|-----|-----|-----|-----|-----|
| Pre-BL  | 10  | 9.7 | 10  | 10  | 9.3 | 10  | 6.0 |
| Pre-GR  | 10  | 8.8 | 8.8 | 8.8 | 5.2 | 10  | 5.5 |
| Post-BL | 9.3 | 7.7 | 9.0 | 8.0 | 8.5 | 5.7 | 6.7 |
| Post-GR | 4.0 | 4.0 | 5.0 | 4.7 | 3.0 | 1.0 | 1.5 |

The broadleaf weeds used in the screening tests were coffeeweed, jimsonweed, tall morningglory, wild mustard, teaweed and velvetleaf, sicklepod and lambsquarters. The grassy weeds used in the screening tests were barnyardgrass, large crabgrass, Johnsongrass, wild oats and yellow foxtail.

Although the invention has been described in considerable detail by the foregoing, it is to be understood that many variations may be made therein by those skilled in the art without departing from the spirit and scope thereof as defined by the appended claims.

I claim:

1. A compound of the formula:

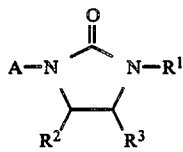

wherein
A is

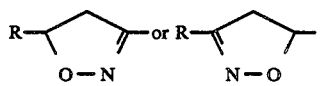

wherein: R is selected from $C_1$ to $C_6$ alkyl, $C_1$ to $C_6$ haloalkyl or up to $C_6$ cycloalkyl; up to $C_5$ alkenyl or alkynyl; $-R^5-O-R^6$ or $-R^5-S-R^6$ wherein $R^5$ is up to $C_6$ alkylene and $R^6$ is $C_1$ to $C_6$ alkyl; or phenyl or benzyl;

$R^1$ is $C_1$ to $C_3$ alkyl or allyl;
$R^3$ is hydrogen;
$R^2$ is

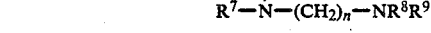

wherein:
$R^7$ is hydrogen or $C_1$ to $C_6$ alkyl or $C_1$ to $C_6$ haloalkyl;
$R^8$ and $R^9$ are the same or different and are selected from hydrogen or $C_1$ to $C_6$ alkyl, $C_1$ to $C_6$ haloalkyl, $C_1$ to $C_6$ alkoxyalkyl, carboxy or $C_1$ to $C_6$ alkyl carbonyl; and
n is 2, 3, 4 or 5.

2. A compound of claim 1 selected from: 3-[5-(t-butyl)-3-isoxazolyl]-1-methyl-4-[N-(2-(dimethylamino)ethyl]amino-2-imidazolidinone; 3-[5-(t-butyl)-3-isoxazolyl]-1-methyl-4-[N-(2-amino)ethyl]-amino-2-imidazolidinone; 3-[5-(t-butyl)-3-isoxazolyl]-1-methyl-4-[N-methyl-N-(2-aminoethyl)]-amino-2-imidazolidinone; 3-[5-(t-butyl)-3-isoxazolyl]-1-methyl-4-[N-(methyl)-N-(2-methylamino)ethyl]amino-2-imidazolidinone; 3-[5-(t-butyl)-3-isoxazolyl]-1-methyl-4-[N-(2-diethylamino)ethyl]amino-2-imidazolidinone; 3-[5-(t-butyl)-3-isoxazolyl]-1-methyl-4-[N-(2-acetylamino)ethyl]amino-2-imidazolidinone; or 3-[5-(t-butyl)-3-isoxazolyl]-1-methyl-4-[N-(2-aminoethyl)-N-ethyl]amino-2-imidazolidinone.

3. A herbicidal formulation containing an inert carrier and herbicidally effective amount of a compound or mixture of compounds defined in claim 1.

4. In a method of controlling weeds the growth of weeds wherein a herbicidally effective amount of herbicide is applied to a growth medium prior to emergence of weeds therefrom or to the weeds subsequent to emergence from the growth medium wherein the improvement resides in using as the herbicide a compound or mixture of compounds as defined in claim 1.

* * * * *

UNITED STATES PATENT OFFICE
CERTIFICATE OF CORRECTION

Patent No. 4,756,744     Dated  July 12, 1988

Inventor(s)  James A. Schwindeman

It is certified that error appears in the above-identified patent and that said Letters Patent is hereby corrected as shown below:

Col. 7, line 25,

"  should read

--  --.

Signed and Sealed this

Twentieth Day of March, 1990

*Attest:*

JEFFREY M. SAMUELS

*Attesting Officer*     *Acting Commissioner of Patents and Trademarks*